United States Patent [19]

Schmidt et al.

[11] Patent Number: 5,053,045
[45] Date of Patent: Oct. 1, 1991

[54] SURGICAL CLIP

[76] Inventors: Ferenc J. Schmidt, 619 Rose La., Bryn Mawr, Pa. 19010; P. Kevin Maughan, 6012 White Heron La., Sanibel, Fla. 33957

[21] Appl. No.: 491,455
[22] Filed: Mar. 9, 1990

Related U.S. Application Data

[63] Continuation-in-part of Ser. No. 245,354, Sep. 16, 1988, abandoned.

[51] Int. Cl.⁵ .............................. A61B 17/12
[52] U.S. Cl. .................... 606/157; 606/155; 606/158
[58] Field of Search ............. 128/325, 326, 334 R, 128/335.5; 606/49, 51, 52, 151, 155, 157, 158

[56] References Cited

U.S. PATENT DOCUMENTS

| | | |
|---|---|---|
| 1,222,510 | 4/1917 | Zirkle . |
| 3,827,438 | 8/1974 | Kees, Jr. . |
| 4,024,868 | 5/1977 | Williams . |
| 4,192,315 | 3/1980 | Hilzinger et al. . |
| 4,340,061 | 7/1982 | Kees, Jr. et al. . |
| 4,360,023 | 11/1982 | Sugita et al. . |
| 4,407,285 | 10/1983 | Perlin . |
| 4,444,187 | 4/1984 | Perlin . |
| 4,484,581 | 11/1984 | Martin et al. . |
| 4,489,725 | 12/1984 | Casey et al. . |
| 4,602,631 | 7/1986 | Furatsu . |
| 4,658,822 | 4/1987 | Kees, Jr. . |
| 4,660,558 | 4/1987 | Kees, Jr. . |
| 4,686,983 | 8/1987 | Leisman et al. . |
| 4,765,335 | 8/1988 | Schmidt et al. . |
| 4,777,949 | 10/1988 | Perlin . |
| 4,777,950 | 10/1988 | Kees, Jr. . |
| 4,796,625 | 1/1989 | Kees, Jr. . |
| 4,827,930 | 5/1989 | Kees, Jr. . |

OTHER PUBLICATIONS

Sugita Aneurysm Clip Spec. Sheet for Temporary Type 1/1 (mm) and Standard Type 1/1 (mm).
Sugita Aneurysm Clip Spec. Sheet for Clip-Applying Forceps and Clip-Remover.

*Primary Examiner*—V. Millin
*Assistant Examiner*—J. Doyle
*Attorney, Agent, or Firm*—Ratner & Prestia

[57] ABSTRACT

A surgical clip formed from a continuous, resilient member and having a coil spring and two arms supporting clamping jaws. The coil spring forces the clamping jaws together. One arm has a guide section, through which the guided element of the second arm extends, to guide and restrict movement of the second arm, thereby correctly engaging the clamping jaws.

39 Claims, 3 Drawing Sheets

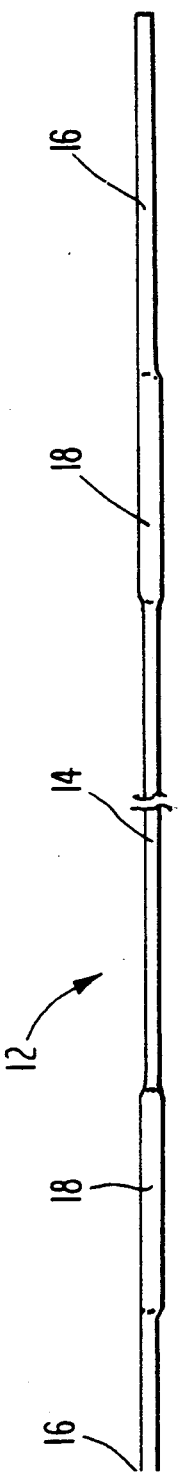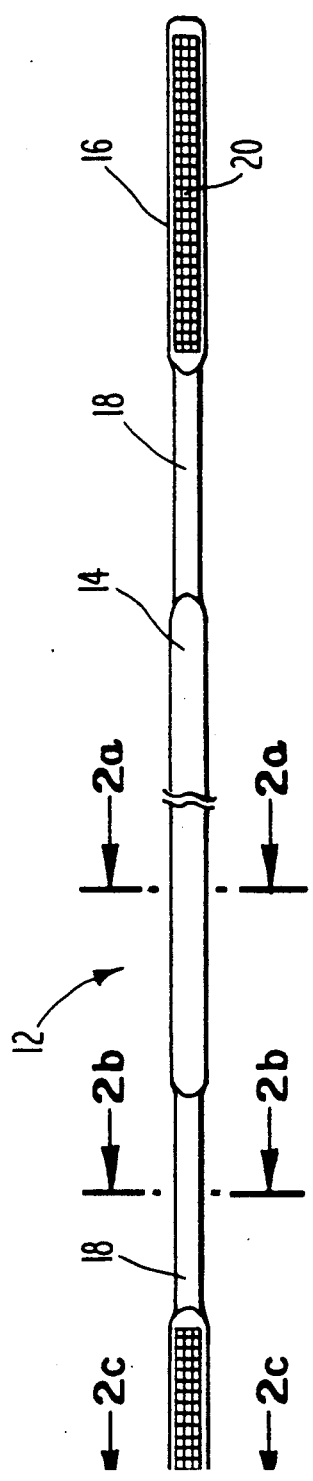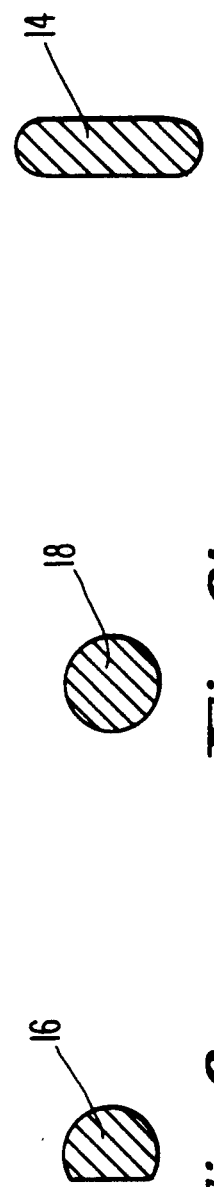

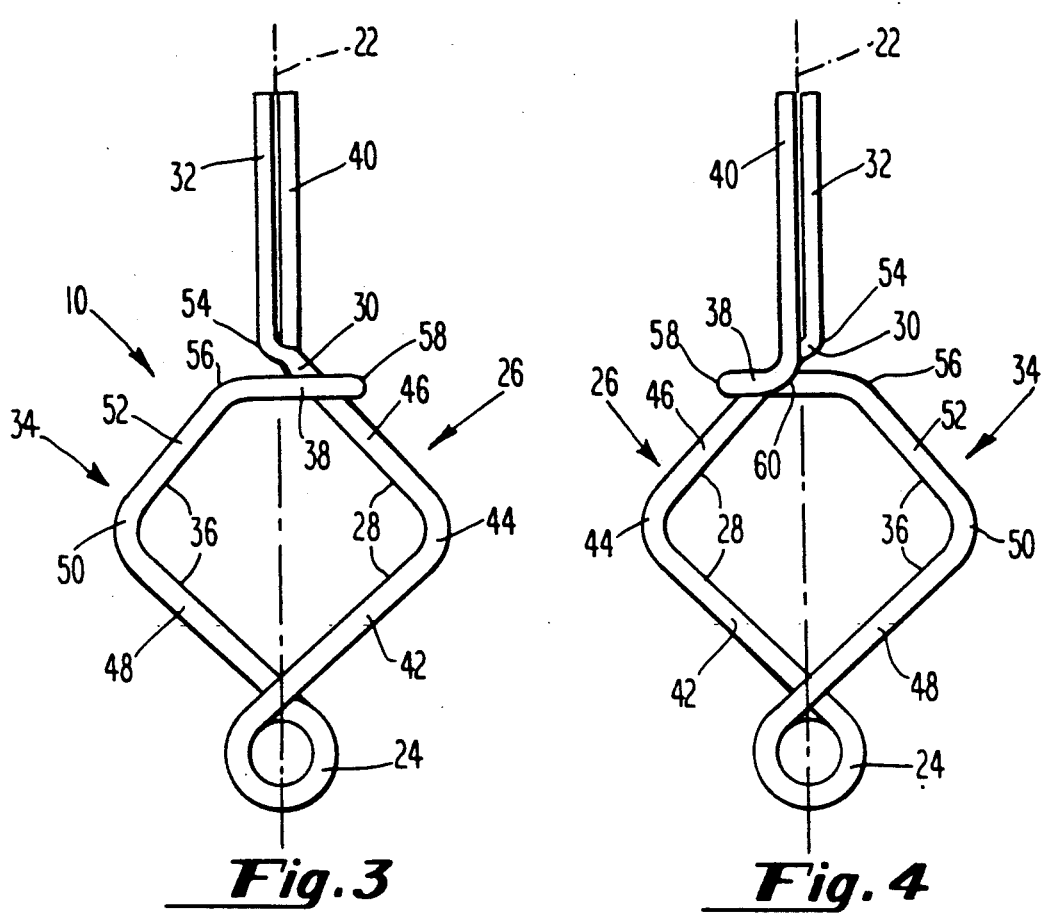
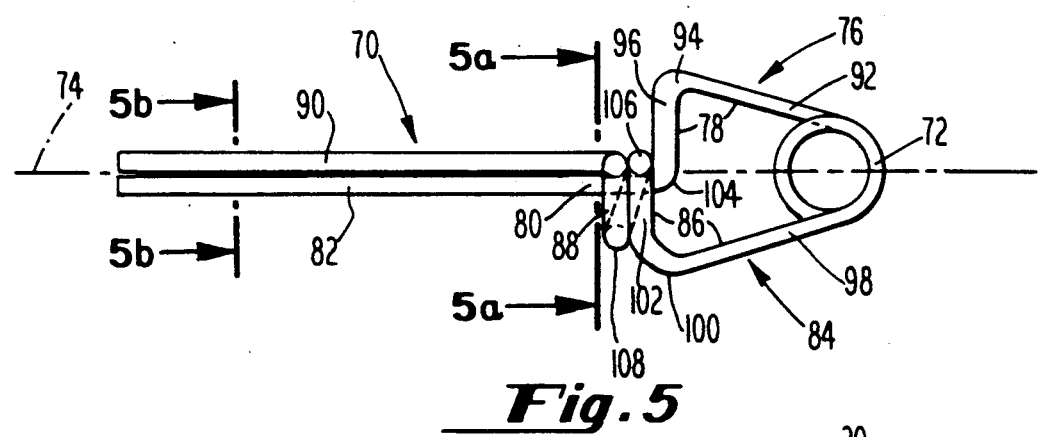
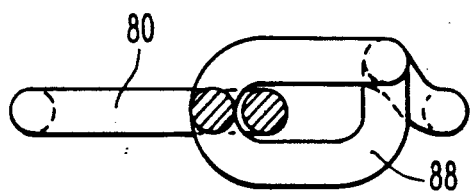 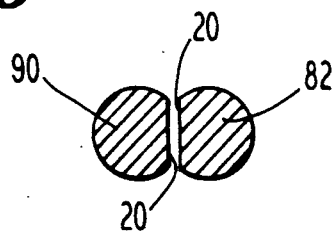

SURGICAL CLIP

BACKGROUND OF THE INVENTION

This application is a Continuation-in-Part of our application serial number 245,354 filed Sept. 16, 1988, which has common inventorship with the present invention.

TECHNICAL FIELD

This invention relates to an improved surgical clip for clamping vascular tissue to, for example, isolate a cerebral aneurysm.

A cerebral aneurysm clip is a surgical instrument which clamps the base part of a cerebral aneurysm to temporarily or permanently isolate it from the cerebral artery. For this purpose, the clip must maintain the clamping pressure with high reliability as long as desired without injury to the wall of the blood vessel. Such injury might be caused, for example, by a shearing action of the clamping jaws, which results from improper jaw alignment; improper clamping pressure; foreign material trapped in cracks and crevices formed in the clip design; surface imperfections on the clip material which can tear tissue; or the use of unsuitable materials to manufacture the clip.

A number of different cerebral aneurysm clips are known in the art. These clips all have shortcomings, however, which render them undesirable for their designed use.

To provide satisfactory and prolonged service when properly implanted, a cerebral aneurysm clip should satisfy most, and preferably all, of the following criteria:

1. The clamping pressure of the jaws of the clip should be sufficient to isolate the aneurysm but not so high as to damage the blood vessel wall during either temporary or permanent implantation;
2. The clamping pressure of the clip should remain constant over time to prevent displacement or slipping of the clip;
3. Because it is so important, the clamping pressure should be susceptible to adjustment following manufacture of the clip;
4. The clip should be as small as possible to facilitate permanent implantation in the brain;
5. The material of construction of the clip should be nonmagnetic to prevent interference with magnetic resonance imaging;
6. The shape of the clip should not obstruct the surgeon's view during implantation;
7. The clip should be designed for ease of implantation with the appropriate application tool;
8. To prevent unintentional tears and pressure points, the surface of the clip should be smooth and jagged edges should be absent;
9. The surface of the clip should be free from cracks, crevices, and similar defects which trap foreign matter and contamination and which are susceptible to propagation by stress corrosion; and
10. Proper jaw alignment should be maintained at all times to prevent shearing of the vascular tissue between the jaws.

The importance of this last criterion, proper jaw alignment, must be emphasized. Available clips generally either are unable to assure such alignment, or while they prevent misalignment, are unable to meet the remaining criteria.

Basic clips having no provision for maintaining jaw alignment, such as are described in U.S. Pat. No. 3,827,438; U.S. Pat. No. 4,024,868; or U.S. Pat. No. 4,340,061, clearly are not acceptable for implantation under the above-listed criteria.

A number of aneurysm clips having differently designed jaw guides to provide proper jaw alignment have been proposed and are available. In attempting to meet the jaw alignment criterion, however, such clips have problems satisfying the other criteria for an acceptable aneurysm clip. U.S. Pat. No. 4,484,581 describes one such clip. That reference discloses a window formed in one arm to confine the movement of a second arm, which passes through the window, in an arrangement similar to an electrical clamp. The window is formed by a recess in the arm and a separate, plate-like bridge. The bridge is welded to the arm and lies over the recess.

Clips having windows are necessarily formed from wide strips of metal to allow for the depth of a recess. Such width both obstructs the surgeon's view and prevents precision clamping of the aneurysm base. When the size of such a clip is reduced to dimensions typical of cerebral implants (~2 mm wide, 0.5-2 cm long), stainless steel must be used to provide adequate strength in the material forming the window recess and in the thinner portion of the second arm passing through that recess. Use of stainless steel can be undesirable for cerebral implantation because its magnetic properties interfere with magnetic resonance imaging diagnosis.

Use of the highly desirable, implant-grade titanium 6-Al 4-V alloy circumvents this objection but presents an additional problem. Typically, the recess in the "window" arm is formed by machining the width of the arm down to less than half of the full width of the arm. The "guided" arm is similarly machined to fit inside the window. This reduction in the width of the arms both weakens the arms and creates stress concentration sites. In addition, titanium metal and its alloys are notch sensitive and susceptible to phase separation when machined. The sharp corners of the recess and the machining process used to form the guide can result in the creation and propagation of microcracks in the metal surface, a possibility which renders this style of clip undesirable for use as a cerebral implant.

A wire guide member is described in U.S. Pat. No. 4,360,023. The wire restricts the movement of the arms in a manner similar to the window in the arm of the clip in U.S. Pat. No. 4,484,581. The method of fixing the wire in the clip consists of drilling two holes in one arm and subsequently riveting the wire ends into these holes. As with the machined regions of the previously described clip, this arrangement is susceptible to microcracks around the holes and also in the regions of riveting. The resultant potential for propagating cracks and trapping unwanted contaminants in the cracks renders this type of clip unsuitable for safe implantation.

U.S. Pat. No. 4,192,315 discloses an aneurysm clip in which the clamping jaws of the clip are supported by arms which cross inside a ring loop. This clip suffers from a number of problems. First, the guide loop protrudes from the clip to create an undesirable obstruction to the surgeon's view. Although the arms of the clip can be narrowed in the crossing region to permit the use of a smaller, less obstructive ring, such a solution compromises the strength of the clip and its ability to maintain a desired clamping pressure. In addition, the ring is necessarily loose to permit free movement of the arms crossing within it; therefore, the ring can fail to guide the clamping jaws with sufficient precision to avoid shearing the tissue between them. Finally, if the clip is formed of highly desirable titanium metal or titanium alloys, welding of the ring poses problems of poor strength and surface irregularities.

The inventors themselves have patented, in U.S. Pat. No. 4,765,335, an aneurysm clip with differently designed jaw guides to provide proper jaw alignment. In one embodiment, a U-shaped bend in one of the arms forms a retaining guide which accommodates sliding motion of the second arm. Although misalignment of the jaws is prevented in one direction, such misalignment is not precluded in the other direction; there is no bridge element across the U-shaped bend to retain the second arm within the "U". In a preferred embodiment, a loop is formed from a separate piece of wire. The wire is threaded through holes drilled in the arm having the bend, then is welded. This embodiment prevents misalignment but fails other criteria for a desirable clip: the loop is made of a separate, smaller diameter (hence, weaker) wire than the arms; the drilled holes weaken the strength of the arm; and the drilling and welding operations create problems similar to those noted above in describing the other patented aneurysm clips.

The aneurysm clip disclosed in U.S. Pat. No. 4,796,625 provides a guide bar and stop member mounted on one of the arms. The guide bar is spaced from the arm to form a guide slot which receives the second arm. If "mounting" involves welding, the elevated temperatures required to weld would alter the temperature-induced characteristics of a clip formed from a material such as titanium or titanium alloy. Moreover, welding is a difficult and expensive manufacturing operation. If "mounting" involves machining the slot, a thicker, heavier starting material must be used to accommodate the slot. Moreover, machining creates undesirable crevices, voids, and microcracks. In either case, the disclosed clip cannot satisfy the criteria required for a desirable clip.

Another drawback of the clip design which is disclosed in U.S. Pat. No. 4,796,625 is its inability to rescue clips manufactured with an unsafe or insufficient clamping pressure. The arms cannot be disengaged because they are retained from horizontal movement by the stop and from vertical movement by the slot; accordingly, the jaw clamping pressure cannot be adjusted following manufacture. Such a disadvantage exists with any clip designed with a stop or "closed" loop which completely prevents disengagement of the arms.

SUMMARY OF THE INVENTION

Accordingly, the object of this invention is to provide a surgical clip which satisfies most, and preferably all, of the criteria stated above for a satisfactory clip capable of long service.

A surgical clip, constructed in accordance with the present invention, is formed from a continuous, resilient member and includes two arms and a coil spring connected to, and located between, the arms. The first arm has (i) a flex section extending along an axis extending along the length of the clip, (ii) a clamping jaw extending from the flex section at one free end of the resilient member, and (iii) a guided element.

The second arm has (i) a flex section which is disposed on the opposite side of the clip axis from the flex section of the first arm and which extends along the clip axis, (ii) a clamping jaw extending from the flex section at the second free end of the resilient member, and (iii) a guide section which confines movement of the guided element at three points, with two of the points positioned in an essentially common plane on one side of the guided element and the third point positioned on the opposite side of that element.

The two flex sections are resiliently deformable from their positions with respect to the clip axis. The coil spring, located between the first and second flex sections, urges the clamping jaws together. In the preferred embodiment of the invention, the clip is formed from a material which is nonmagnetic and compatible with body tissue, such as titanium or a titanium alloy.

The way in which the foregoing object and other objects are achieved by this invention will become more apparent from the following detailed description and the appended claims when read in conjunction with the accompanying drawings. The drawings have not been drafted to scale, and clearances have been exaggerated to assure clarity.

BRIEF DESCRIPTION OF THE DRAWINGS

In the accompanying drawings:

FIGS. 1 and 2 are top and side views, respectively, of a single, continuous, resilient member from which the various embodiments of the surgical clip of the present invention can be formed;

FIGS. 2a, 2b, and 2c are cross-sectional views taken, respectively, along lines 2a, 2b, and 2c in FIG. 2;

FIGS. 3 and 4 are top and bottom views, respectively, of a first embodiment of a surgical clip constructed in accordance with the present invention;

FIG. 5 shows a top view of a second embodiment of a surgical clip constructed in accordance with the present invention;

FIGS. 5a and 5b are cross-sectional views taken, respectively, along lines 5a and 5b in FIG. 5;

DETAILED DESCRIPTION OF THE INVENTION

Figure 6:
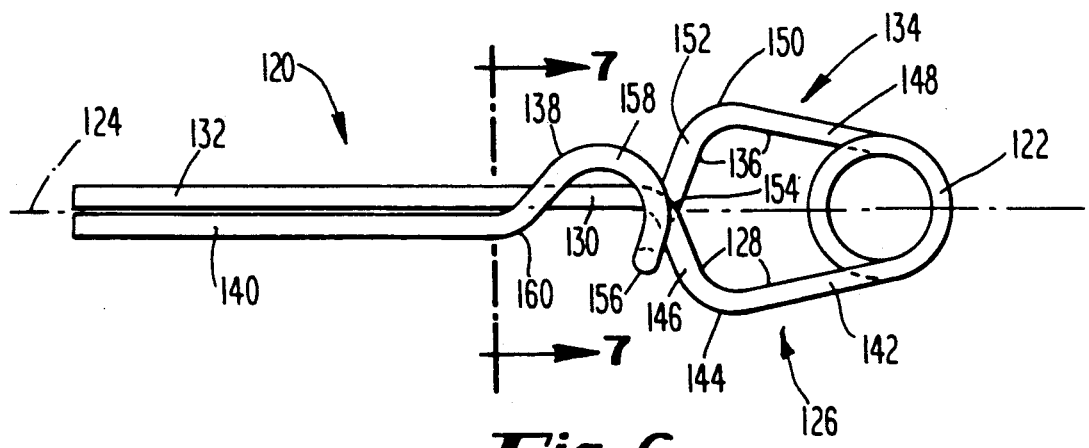
FIG. 6 illustrates a bottom view of a third embodiment of a surgical clip constructed in accordance with the present invention.

Referring to the drawings, a surgical clip 10, constructed in accordance with one embodiment of the present invention, is shown in FIGS. 3 and 4. A second embodiment is shown in FIG. 5. A third embodiment, having three alternatives, is shown in FIGS. 6-9. All embodiments and their alternatives are formed from a single, continuous, resilient member 12 such as shown in FIGS. 1 and 2.

Turning first to FIGS. 1 and 2, member 12 is initially a round wire, preferably of titanium or a titanium alloy. A 2.5-inch long wire of 0.037-inch diameter is suitable, as an example. Member 12 is formed into the three, differently shaped sections shown in the figures: a center section 14 (of about 0.65 inches in length, for example) is used to form coil spring 24, two end sections 16 are used to form clamping jaws 32 and 40, and two connecting wire sections 18 are used to form the remaining elements of clip 10. The point which forms one end of clip 10 is chosen, using the example dimensions, at a position about 1.05 inches from one end of member 12. An off-center position is chosen because first arm 26 requires fewer turns that second arm 34 and the two arms should end at the same point.

As shown in FIG. 2a, center section 14 is flattened, creating an oval from which coil spring 24 is formed. Suitable dimensions for the oval are 0.020 inches by 1.050 inches. Connecting sections 18 retain the round-wire shape, as shown in FIG. 2b and, thus, in the example used, remain circular with a diameter of 0.037 inches. End sections 16 are formed, as shown in FIG. 2c, with flat faces 20 to grasp tissue between the two faces. Faces 20 may be 0.040-inches wide and the maximum depth from face 20 to the apex of the curved portion of section 16 is then 0.032 inches. All of the dimensions provided above are examples only, based on the starting size of the member 12 chosen to form a typically sized surgical clip. Different dimensions are necessary, of course, to form differently sized clips. The size of member 12 must be sufficiently small, of course, to form a clip suitable for cerebral implantation.

First Embodiment

According to one embodiment of the present invention, shown in FIGS. 3 and 4, surgical clip 10 is formed from member 12 along a longitudinal clip axis 22. Coil spring 24 lies on axis 12 at one end of clip 10. A first arm 26 extends away from spring 24, and comprises a first flex section 28, a guided element 30, and a first clamping jaw 32. A second arm 34 also extends away from spring 24, in a direction away from first arm 26, and comprises a second flex section 36, a guide section 38, and a second clamping jaw 40. Spring 24 is located between first flex section 28 and second flex section 36 so that it may urge first clamping jaw 32 and second clamping jaw 40, which are positioned at opposite ends of resilient member 12, against each other.

First flex section 28 extends from spring 24 and is disposed lengthwise along axis 22. Flex section 28 includes a first straight length 42 integrally connected at one end to spring 24. First length 42 extends away from spring 24 at an oblique angle to axis 22 and is integrally connected to a first forcepsgripping elbow 44 at its opposite end. Flex section 28 also includes a second straight length 46 integrally connected at one end to first elbow 44 and integrally connected to guided element 30 at its opposite end, extending toward guided element 30 at an oblique angle to axis 22.

First flex section 28 thus forms a first forceps-gripping elbow 44 at the point in first arm 26 farthest from axis 22. When a force is placed on first elbow 44 directed toward axis 22, elbow 44 moves toward axis 22, causing first clamping jaw 32, which is located on the opposite side of axis 22 from flex section 28, to move away from second clamping jaw 40. When that force is removed, first elbow 44 returns to its initial position farthest from axis 22 and, consequently, first clamping jaw 32 returns to meet second clamping jaw 40. In this way, flex section 28 is resiliently deformable from its position with respect to axis 22.

Second flex section 36, identical to flex section 28, extends from spring 24 and is disposed lengthwise along axis 22 symmetrically with respect to flex section 28 about axis 12. Flex section 36 includes a third straight length 48 integrally connected at one end to spring 24. Third length 48 extends away from spring 24 at an oblique angle to axis 22 and is integrally connected to a second forceps-gripping elbow 50 at its opposite end. Flex section 36 also includes a fourth straight length 52 integrally connected at one end to second elbow 50 and integrally connected to guide section 38 at its opposite end, extending toward guide section 38 at an oblique angle to axis 22.

Second flex section 36 thus forms a second forceps-gripping elbow 50 at the point in second arm 34 farthest from axis 22. When a force is placed on second elbow 50 directed toward axis 22, elbow 50 moves toward axis 22, causing second clamping jaw 40, which is located on the opposite side of axis 22 from flex section 36, to move away from first clamping jaw 32. When that force is removed, second elbow 50 returns to its initial position farthest from axis 22 and, consequently, second clamping jaw 40 returns to meet first clamping jaw 32. In this way, flex section 36 is resiliently deformable from its position with respect to axis 22.

Guided element 32 of first arm 26 is integrally connected to first flex section 28 on one end and to first clamping jaw 32 on its opposite end. Element 30 makes a simple turn 54 of less than 180 degrees between first elbow 44 of flex section 28 and jaw 32, extending through guide section 38 of second arm 34 and across axis 22.

Bent guide section 38 of second arm 34 is integrally connected to second flex section 36 on one end and to second clamping jaw 40 on its opposite end. Guide section 38 makes a bend 56 before crossing axis 22. Guide section 38 extends from flex section 36 generally perpendicular to axis 22 after making bend 56, crosses axis 22, and passes over guided element 30. At the point where guide section 38 is directly over guided element 30, section 38 and element 30 nearly, but do not, contact. Thus, element 32 is confined by section 38 and cannot move upward.

Section 38 then makes a reverse twist 58 which goes around guided element 30 so that section 38 is now underneath element 32 and directed substantially perpendicularly back toward axis 22. Reverse twist 58 is located so that jaws 32 and 40, when urged toward each other, will contact before guided element 32 would contact the inside surface of twist 58. For the embodiment of the invention illustrated in FIGS. 3 and 4, guide section 38 is open; it does not completely encircle guided element 30.

After passing underneath element 30, section 38 makes a substantially perpendicular, L-shaped pivot 60 so that section 38 passes underneath element 30 a second time. At the two points where guide section 38 is directly under guided element 30, section 38 and element 30 nearly, but do not, contact. Thus, element 30 is confined by section 38 and cannot move downward. The two points lie in an essentially common plane underneath element 30 on the opposite side of element 32 from the near-contact, movement-confining point over element 30.

Coil spring 24, located between straight lengths 42 and 48 of arms 26 and 34, respectively, urges flex sections 28 and 36 apart and clamping jaws 32 and 40 together with a predetermined force. For the first embodiment of the invention illustrated in FIGS. 3 and 4, clamping jaws 32 and 40 are disposed on opposite sides of axis 22. Clamping jaws 32 and 40 are separated and moved away from axis 22 by application of a force, using an appropriate tool such as a forceps, to elbows 44 and 50. The force draws elbows 44 and 10 toward one another against the action of spring 24. When the separated clamping jaws 32 and 40 are properly positioned around the tissue to be clamped, the force applied to elbows 44 and 50 is released and coil spring 24 urges jaws 32 and 40 together with the tissue clamped between them.

Guide section 38 of the first embodiment illustrated in FIGS. 3 and 4 is "open": section 38 does not encircle guided element 30. Thus, because section 38 does not limit the maximum opening of jaws 32 and 40, it is possible to apply a sufficiently strong force to elbows 44 and 50 so that guided element 30 exits guide section 38 completely This allows the manufacturer the freedom to disengage jaws 32 and 40 after clip 10 has been manufactured and to readjust the jaw-closing force required by choosing a new angled position for jaws 32 and 40. That procedure reduces or eliminates manufacturing rejects caused by improper closing clip force.

Adjustment of the jaw-closing force is an advantage because, as indicated above, such force must be sufficient to clamp tissue effectively yet insufficient to cause injury to that tissue. Note that the force required to cause guided element 30 to exit guide section 38 completely is greater than the force normally applied by the applicator (forceps) during operation of clip 10 to overcome the spring force and to enclose tissue. Thus, during operation following manufacture, guided element 30 remains confined within guide section 38 by the three points of near-contact between element 30 and section 38.

Also as indicated above, misalignment of jaws 32 and 40, when closing clip 10 or with clip 10 in the clamped position, is undesirable. Such misalignment may cause jaws 32 and 40 to damage the clamped tissue by shearing that tissue or may reduce the clamping force to an ineffective magnitude. The three points of near-contact between element 30 and section 38 function to prevent misalignment of jaws 32 and 40 by limiting guided element 30 to two degrees of freedom within guide section 38. As element 30 slides along the length of guide section 38 during opening and closing of clip 10, the three points of near-contact maintain element 32 within the confines of section 38 and in a horizontal direction (two degrees of freedom). Guided element 30 cannot move either up or down out of the horizontal plane; if element 32 is urged either up or down, element 32 immediately contacts guided element 38 at one or more of the three points of (previously) near-contact. Thus, guided element 30 is permitted only two degrees of freedom to move, assuring alignment of jaws 32 and 40 during placement and implantation of clip 10.

Second Embodiment

FIG. 5 shows a second embodiment of a surgical clip constructed in accordance with the present invention. This embodiment of the invention is generally similar to the first embodiment of the invention shown in FIGS. 3 and 4, except that the guide section in the second embodiment is formed differently from the guide section in the first embodiment.

As with the surgical clip illustrated in FIGS. 3 and 4, the surgical clip 70, shown in FIG. 5 is formed from a single, continuous, resilient member 12 such as is shown in FIGS. 1 and 2.

Coil spring 72 lies on axis 74 at one end of clip 70. A first arm 76 extends away from spring 72 and comprises a first flex section 78, a guided element 80, and a first clamping jaw 72. A second arm 84 also extends away from spring 72, in a direction away from first arm 76, and comprises a second flex section 76, a guide section 88, and a second clamping jaw 90. Spring 72 is located between first flex section 72 and second flex section 26 so that it may urge first clamping jaw 72 and second clamping jaw 90, which are positioned at opposite ends of resilient member 12, against each other.

First flex section 78 extends from spring 72 and is disposed lengthwise along axis 74. Flex section 72 includes a first straight length 92 integrally connected at one end to spring 72. First length 92 extends away from spring 72 at an oblique angle to axis 74 and is integrally connected to a first forceps-gripping elbow 94 at its opposite end. Flex section 72 also includes a second straight length 96 integrally connected at one end to first elbow 94 and integrally connected to guided element so at its opposite end.

First flex section 78 thus forms a first forceps-gripping elbow 94 at the point in first arm 76 farthest from axis 74. When a force is placed on first elbow 94 directed toward axis 74, elbow 94 moves toward axis 74, causing first clamping jaw 82, which is located on the opposite side of axis 74 from flex section 72, to move away from second clamping jaw 90. When that force is removed, first elbow 94 returns to its initial position farthest from axis 74 and, consequently, first clamping jaw 82 returns to meet second clamping jaw 90. In this way, flex section 72 is resiliently deformable from its position with respect to axis 74.

Second flex section 86, substantially identical to flex section 72, extends from spring 72 and is disposed lengthwise along axis 74 substantially symmetrically with respect to flex section 78 about axis 74. Flex section 76 includes a third straight length 98 integrally connected at one end to spring 72. Third length 98 extends away from spring 72 at an oblique angle to axis 74 and is integrally connected to a second forceps-gripping elbow 100 at its opposite end. Flex section 86 also includes a fourth straight length 102 integrally connected at one end to second elbow 100 and integrally connected to guide section 22 at its opposite end.

Second flex section 76 thus forms a second forceps-gripping elbow 100 at the point in second arm 84 farthest from axis 74. When a force is placed on second elbow 100 directed toward axis 74, elbow 100 moves toward axis 74, causing second clamping jaw 90, which is located on the opposite side of axis 74 from flex section 86, to move away from first clamping jaw 82. When that force is removed, second elbow 100 returns to its initial position farthest from axis 74 and, consequently, second clamping jaw 90 returns to meet first clamping jaw 82. As shown in FIG. 5b, jaws 82 and 90 are aligned so that flat faces 20 meet. In this way, flex section 86 is resiliently deformable from its position with respect to axis 74.

Guided element 80 of first arm 76 is integrally connected to first flex section 72 on one end and to first clamping jaw 82 on its opposite end. Element 80 makes a simple turn 104 of less than 180 degrees between first elbow 94 of flex section 72 and jaw 72, extending through guide section 72 of second arm 74 and across axis 74.

Bent guide section 78 of second arm 74 is integrally connected to second flex section 86 on one end and to second clamping jaw 90 on its opposite end. Guide section 72 extends from flex section 86 and crosses axis 74 substantially perpendicular to axis 74. Section 22 passes over guided element 80 and, at the point where guide section 22 is directly over guided element so, section 88 and element 80 nearly, but do not, contact. Thus, element so is confined by section 88 and cannot move upward. Guide section 22 then makes a first reverse bend 106 and passes back across, at about a forty-five degree angle to, axis 74 and underneath element so. At the point where guide section 82 is directly under guided element so, section 22 and element so nearly, but do not, contact. Thus, element so is confined by section 22 and cannot move downward.

Guide section 88 then makes a second reverse bend 108 so that section 88 is directed back toward axis 74 perpendicular to axis 74. Guide section 22 again passes over guided element so, creating a point where section 22 and element so nearly, but do not, contact. Thus, element 80 is confined by a second point which prevents section 22 from upward movement. The two points lie in an essentially common plane on top of element 80 on the opposite side of element so from the near-contact, movement-confining point under element 80.

As best shown in FIG. 5a, guide section 88 forms a flattened, oval, loop which encircles guided element 80. Guide section 22 is shaped and dimensioned so that guided element so, extending through the oval loop formed, can slide within the confines of the loop but is prevented from upward or downward movement by the points of near contact defined by the loop.

Coil spring 72, located between straight lengths 92 and 98 of arms 76 and 84, respectively, urges flex sections 72 and 16 apart and clamping jaws 82 and 90 together with a predetermined force. For the second embodiment of the invention illustrated in FIG. 5, clamping jaws 82 and 90 are disposed on opposite sides of axis 74. Clamping jaws 88 and 90 are separated and moved away from axis 74 by application of a force, using an appropriate tool such as a forceps, to elbows 94 and 100. The force draws elbows 94 and 100 toward one another against the action of spring 72. When the separated clamping jaws 82 and 90 are properly positioned around the tissue to be clamped, the force applied to elbows 94 and 100 is released and coil spring 72 urges jaws 82 and 90 together with the tissue clamped between them.

First reverse bend 106 is located so that guided element so does not contact the inside surface of bend 106 when clamping jaws 82 and 90 are urged together toward their closed position. Similarly, second reverse bend 108 is located so that guided element so does not contact the inside surface of bend 108 when jaws 82 and 90 are urged apart to enclose tissue.

Guide section 22 of the second embodiment illustrated in FIG. 5 is "closed": section 72 completely encircles guided element so. Thus, section 72 limits the maximum opening of jaws 82 and 90 and it is impossible for guided element 80 to exit guide section 88 completely. Although the design of this second embodiment does not allow the manufacturer the freedom to disengage jaws 82 and 90 after clip 70 has been manufactured and to readjust the jaw-closing force required, it does assure permanent alignment of jaws 82 and 90.

The embodiment of the invention shown in FIG. 5, in which guide section 88 is substantially perpendicular to axis 74, has several advantages over an alternative surgical clip in which the loop of guide section 22 is not perpendicular to axis 74. In such a clip, guide section 88 would extend from flex section 86 and cross axis 74 at an oblique angle to axis 74; section 22 would be oriented at an oblique angle to axis 74 at the points of near contact. One advantage of the embodiment shown in FIG. 5 is that the perpendicular bends require less lengthwise distance than an obliquely oriented loop to complete the necessary turns. Thus, a shorter clip 70 is possible using the perpendicular orientation of FIG. 5. Another advantage of the perpendicular loop is that it tends less to obscure the surgeon's view during implantation.

Third Embodiment

FIGS. 6, 7, 8, and 9 show a third embodiment of a surgical clip constructed in accordance with the present invention. Three alternatives to the third embodiment are illustrated, one in FIGS. 6 and 7, another in FIG. 8, and the third in FIG. 9. This embodiment of the invention is generally similar to the first two embodiments of the invention shown in FIGS. 3 through 5, except that the guide section in the third embodiment is formed differently from the guide sections of the first and second embodiments.

As with the surgical clips illustrated in FIGS. 3 through 5, the surgical clip 120, shown in FIGS. 6, 7, 8, and 9, is formed from a single, continuous, resilient member 12 such as is shown in FIGS. 1 and 2.

Coil spring 122 lies on axis 124 at one end of clip 120. A first arm 126 extends away from spring 122 and comprises a first flex section 128, a guided element 130, and a first clamping jaw 132. A second arm 134 also extends away from spring 122, in a direction away from first arm 126, and comprises a second flex section 136, a guide section 138, and a second clamping jaw 140. Spring 122 is located between first flex section 128 and second flex section 136 so that it may urge first clamping jaw 132 and second clamping jaw 140, which are positioned at opposite ends of resilient member 12, against each Other.

First flex section 128 extends from spring 122 and is disposed lengthwise along axis 124. Flex section 128 includes a first straight length 142 integrally connected at one end to spring 122. First length 142 extends away from spring 122 at an oblique angle to axis 124 and is integrally connected to a first forceps-gripping elbow 144 at its opposite end. Flex section 128 also includes a second straight length 146 integrally connected at one end to first elbow 144 and integrally connected to guided element 130 at its opposite end, extending toward guided element 130 at an oblique angle to axis 124.

First flex section 128 thus forms a first forceps-gripping elbow 144 at the point in first arm 126 farthest from axis 124. When a force is placed on first elbow 144 directed toward axis 124, elbow 144 moves toward axis 124, causing first clamping jaw 132, which is located on the opposite side of axis 124 from flex section 128, to move away from second clamping jaw 140. When that force is removed, first elbow 144 returns to its initial position farthest from axis 124 and, consequently, first clamping jaw 132 returns to meet second clamping jaw 140. In this Way, flex section 128 is resiliently deformable from its position with respect to axis 124.

Second flex section 136, substantially identical to flex section 128, extends from spring 122 and is disposed lengthwise along axis 124 substantially symmetrically with respect to flex section 128 about axis 124. Flex section 136 includes a third straight length 48 integrally connected at one end to spring 122. Third length 148 extends away from spring 122 at an oblique angle to axis 124 and is integrally connected to a second forceps-gripping elbow 150 at its opposite end. Flex section 136 also includes a fourth straight length 152 integrally connected at one end to second elbow 150 and integrally connected to guide section 138 at its opposite end, extending toward guide section 138 at an oblique angle to axis 124.

Second flex section 136 thus forms a second forceps-gripping elbow 150 at the point in second arm 134 farthest from axis 124. When a force is placed on second elbow 150 directed toward axis 124, elbow 150 moves toward axis 124, causing second clamping jaw 140, which is located on the opposite side of axis 124 from flex section 136, to move away from first clamping jaw 132. When that force is removed, second elbow 150 returns to its initial position farthest from axis 124 and, consequently, second clamping jaw 140 returns to meet first clamping jaw 132. In this Way, flex section 136 is resiliently deformable from its position with respect to axis 124.

Guided element 130 of first arm 126 is integrally connected to first flex section 128 on one end and to first clamping jaw 132 on its opposite end. Element 130 makes a simple turn 154 of less than 180 degrees between first elbow 144 of flex section 128 and jaw 132, extending through guide section 138 of second arm 134 and across axis 124.

Bent guide section 138 of second arm 134 is integrally connected to second flex section 136 on one end and to second clamping jaw 140 on its opposite end.

Guide section 138 extends from flex section 136 and crosses axis 124 at an oblique angle to axis 124. Section 138 passes over guided element 130 and, at the point where guide section 138 is directly over guided element 130, section 138 and element 130 nearly, but do not, contact. Thus, element 130 is confined by section 138 and cannot move upward.

The distinction between the three alternatives to the third embodiment lies in the shape of guide section 138 after it has formed the near-contact point over guided element 130.

In the first alternative, shown in FIG. 6, guide section 138 then makes a reverse twist 156 which goes around guided element 130 so that section 138 is now underneath element 130 and directed back toward axis 124 at virtually the same oblique angle at which section 132 originally crossed axis 124 when above element 130 Reverse twist 156 is located so that jaws 132 and 140, when urged toward each other, will contact before guided element 130 would contact the inside surface of twist 156.

Guide surface 138 then forms a gradual, C-shaped loop 158 underneath guided element 132. Loop 158 crosses axis 124 twice. At the two points Where loop 158 of guide section 138 is directly under guided element 130, section 138 and element 130 nearly, but do not, contact. The two points lie in an essentially common plane underneath element 130 on the opposite side of element 130 from the near-contact, movement-confining point on top of element 130. Thus, element 130 is confined by section 138 and cannot move downward. Guide section 138 then makes a final bend 160 so that section 138 is directed parallel to axis 124 and integrally connects with jaw 140. The manner in which guide section 138 confines guided element 130 is illustrated more specifically in FIG. 7.

This first alternative embodiment is the most elegant of the three alternatives shown. It is also the most difficult to manufacture, however, because the tight turns and changing orientations required of guide section 138 are not easily formed. Moreover, reverse twist 156 presents a relatively sharp corner, absent in the other two alternatives, which risks the undesirable result of creating and propagating microcracks in the metal surface.

Figure 8:
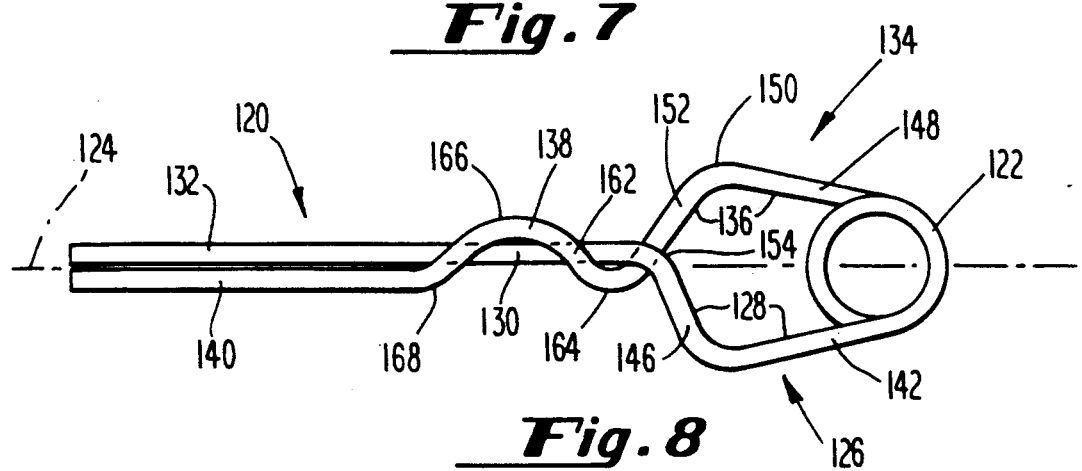
FIG. 8 is a bottom view of an alternative third embodiment, with the distance separating the points of near contact between the guided element and guide section elongated relative to the alternative embodiment shown in FIG. 6, of a surgical clip constructed in accordance with the present invention.

In the second alternative of the third embodiment, shown in FIG. 8, guide section 138 makes an S-shaped curve 162 after it has formed the near-contact point over guided element 130. Curve 162 is composed of two, oppositely faced, integral, C-shaped loops 164 and 166. First loop 164 goes around guided element 130 so that curve 162 of section 138 is now underneath element 130 and directed back toward axis 124. First loop 164 is located so that jaws 132 and 140, when urged toward each other, will contact before guided element 130 would contact the inside surface of loop 164.

Second loop 166 Of curve 162 lies in a single plane underneath guided element 130 and crosses axis 124 twice. At the two points where loop 166 of curve 162 of guide section 138 is directly under guided element 132, section 138 and element 130 nearly, but do not, contact. The two points lie in an essentially common plane underneath element 130 on the opposite side of element 130 from the near-contact, movement-confining point on top of element 130. Thus, element 130 is confined by section 138 and cannot move downward. Guide section 138 then makes a final bend 168 so that section 138 is directed parallel to axis 124 and integrally connects with jaw 140.

Figure 7:
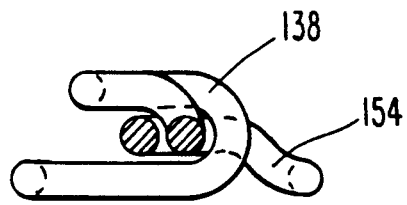
FIG. 7 is a cross-sectional view taken along line 7 in FIG. 6.

The second alternative embodiment of FIG. 8 extends or lengthens the two points of near-contact underneath element 130 relative to the first alternative of FIGS. 6 and 7. Thus, S-shaped curve 162 requires a loaner clip to complete its turns than does loop 158 of the first alternative. The second alternative is less desirable, therefore, for smaller clip sizes—although it is easier to manufacture than the first alternative shown.

Figure 9:
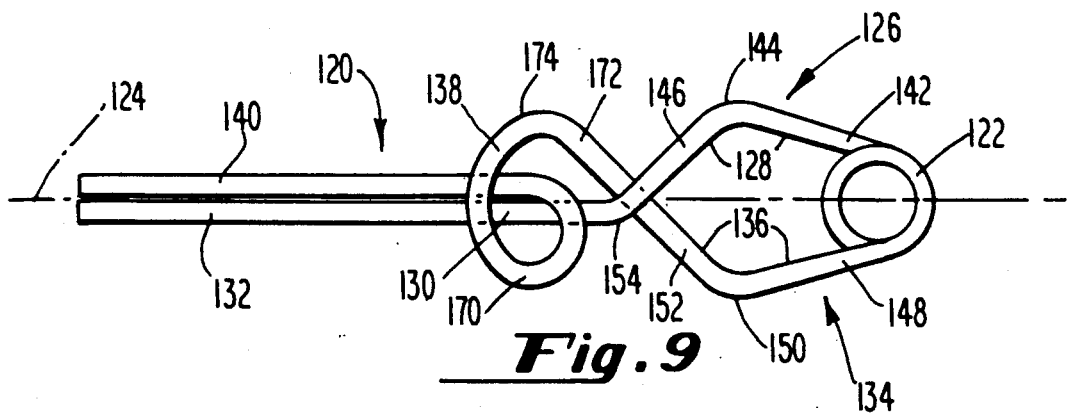
FIG. 9 is a bottom view of another alternative third embodiment, in which the guide element makes a full spiral on one side of the guided element, of a surgical clip constructed in accordance with the present invention.

In the final alternative of the third embodiment shown, in FIG. 9, guide section 138 makes a full spiral 170 underneath guided element 130. After it has crossed axis 124 and formed the near-contact point over guided element 130, guide section 138 continues away from axis 124, forming straight extension 172, at an oblique angle to axis 124. Extension 172 of section 138 ends in a bow 174 which turns section 138 back toward axis 124 and which integrally connects to spiral 170.

Extension 172 and bow 174 cause section 138 to go around guided element 132 so that section 138 is now underneath element 130 and directed back toward axis 124. Extension 172 and bow 174 are located so that jaws 132 and 140, when urged toward each other, will contact before guided element 130 would contact the inside surface of either extension 172 or bow 174.

Spiral 170 crosses axis 124 twice. At the two points where spiral 170 of guide section 138 is directly under guided element 130, section 138 and element 130 nearly, but do not, contact. The two points lie in an essentially common plane underneath element 130 on the opposite side of element 132 from the near-contact, movement-confining point on top of element 130. Thus, element 130 is confined by section 138 and cannot move downward.

Like S-shaped curve 162 of the second alternative shown in Figure B, spiral 170 of the third alternative requires a longer clip to complete its turns than does loop 158 of the first alternative. The third alternative is less desirable, therefore, for smaller clip sizes than is the first alternative. The third alternative of clip 120 is the easiest of the three alternatives shown to manufacture, because the smoothly flowing spiral is easy to fixture.

Coil spring 122, located between straight lengths 142 and 148 of arms 126 and 134, respectively, urges flex sections 128 and 136 apart and clamping jaws 132 and 140 together with a predetermined force. For the third embodiment of the invention illustrated in FIGS. 6, 7, 8, and 9, clamping jaws 132 and 140 are disposed on opposite sides of axis 124. Clamping jaws 132 and 140 are separated and moved away from axis 124 by application of a force, using an appropriate tool such as a forceps, to elbows 144 and 150. The force draws elbows 144 and 150 toward one another against the action of spring 122. When the separated clamping jaws 132 and 140 are properly positioned around the tissue to be clamped, the force applied to elbows 144 and 150 is released and coil spring 122 urges jaws 132 and 140 together with the tissue clamped between them.

Guide section 138 of the third embodiment illustrated in FIGS. 6, 7, 8, and 9 is "open": section does not encircle guided element 130 completely. Thus, because section 138 does not limit the maximum opening of jaws 132 and 140, it is possible to apply a sufficiently strong force to elbows 144 and 150 so that guided element 130 exits guide section 138. This allows the manufacturer the freedom to disengage jaws 132 and 140 after clip 120 has been manufactured and to readjust the jaw-closing force required by choosing a new angled position for jaws 132 and 140. That procedure reduces or eliminates manufacturing rejects caused by improper closing clip force.

Note that the force required to cause guided element 130 to exit guide section 138 completely is greater than the force normally applied by the applicator (forceps) during operation of clip 120 to overcome the spring force and to enclose tissue. Thus, during operation following manufacture, guided element 130 remains confined within guide section 138 by the three points of near-contact between element 130 and section 138.

The three points of near-contact between element 130 and section 138 also function to prevent misalignment of jaws 132 and 140 by limiting guided element 130 to two degrees of freedom within guide section 138. As element 130 slides along the length of guide section 138 during opening and closing of clip 120, the three points of near-contact maintain element 130 within the confines of section 138 and in a horizontal direction (two degrees of freedom). Guided element 130 cannot move either up or down out of the horizontal plane; if element 130 is urged either up or down, element 130 immediately contacts guided element 138 at one or more of the three points of (previously) near-contact. Thus, guided element 130 is permitted only two degrees of freedom to move, assuring alignment of jaws 132 and 140 during placement and implantation of clip 120.

Comparing the third embodiment of the invention shown in FIGS. 6, 7, 8, and 9 with the first embodiment described above and illustrated in FIGS. 3 and 4, it is apparent that both embodiments are "open" designs. The third embodiment avoids the substantially perpendicular, L-shaped pivot 62 of the first embodiment. Accordingly, the third embodiment, with its more gradual turns, is easier to manufacture and carries less risk to notch sensitive metals like titanium and alloys of titanium. On the other hand, the turns of the first embodiment require less space and, therefore, are more suitable for smaller-sized clips.

In the preferred embodiments of the present invention, resilient member 12 is made from titanium metal or a titanium alloy. The metal or alloy are nonmagnetic, thus preventing interference with magnetic resonance imaging of the body. The metal or alloy are also inert and biocompatible with body tissue and fluid. The Ti-6 Al-4 V alloy is suitable. Other materials which have the desired properties can be used, however, for a clip made in accordance with the present invention. In fact, because the invention does not require welding, drilling, or machining sharp corners, a wider variety of materials may be suitable than for the previously known clips.

In addition, a surgical clip constructed in accordance with the present invention may take other forms, from the embodiments described and illustrated, to suit the particular needs of an application. Specifically, clips which are merely mirror images of the drawings shown are possible.

The two clamping jaws preferably are substantially straight, symmetrical about the clip axis, and of approximately equal length so that the two free ends of resilient member 12 terminate at the same point along the clip axis. Each jaw preferably presents a flat face toward its counterpart for contacting and clamping tissue between them. Alternatively, the jaws themselves may be curved or shaped to suit the shape and location of the tissue to be clamped. The jaws may be oriented at an angle or may parallel each other, depending upon the requirements of the clip placement.

Although only preferred embodiments of the invention have been specifically illustrated and described above, it should be understood that various alternatives may be devised by those of ordinary skill in the art without departing from the spirit and scope of the present invention as defined in the appended claims.

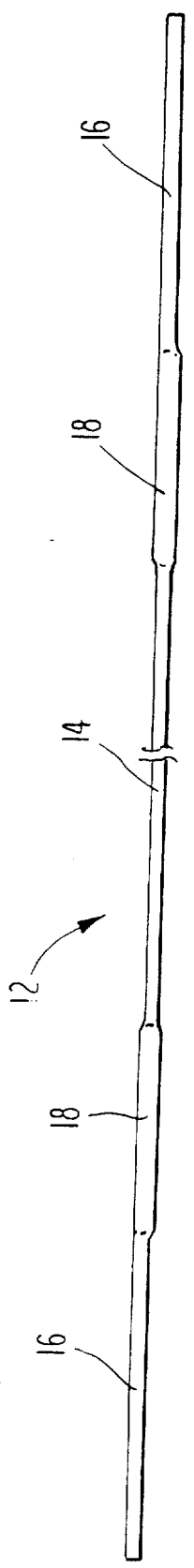
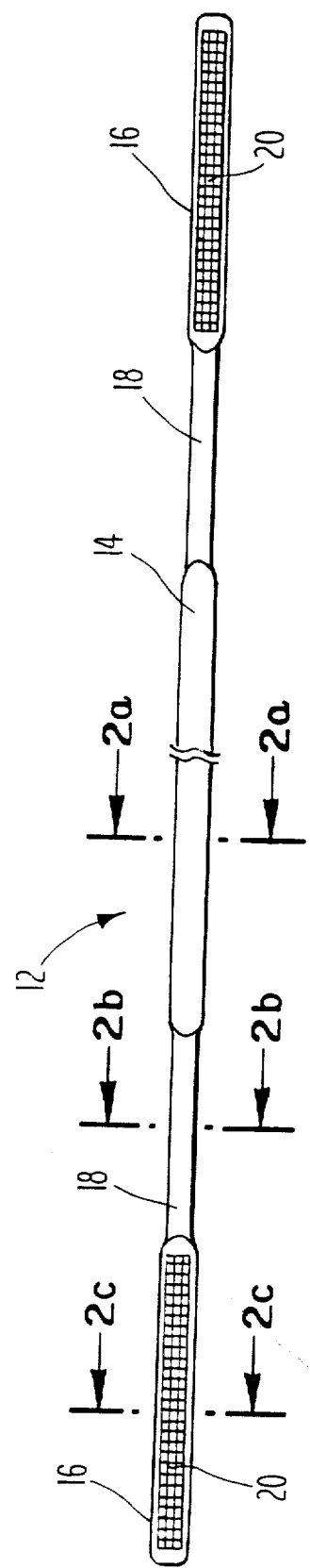
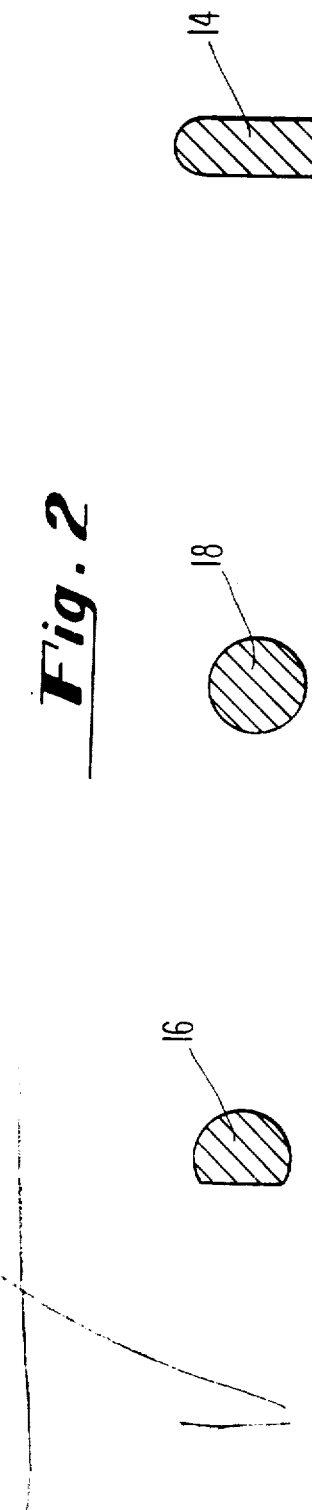

What is claimed is:

1. A surgical clip comprising a single, continuous, resilient member formed along a clip axis without machining operations which remove material or joining operations which add material and including:
   a coil spring positioned on the axis and at one end of said clip;
   a first arm having
   (i) a first flex section extending from said spring away from said clip axis to a point farthest from said clip axis then toward said clip axis so that said first flex section is disposed lengthwise along said clip axis, resiliently deformable from its position with respect to said clip axis, and forming a first forceps-gripping elbow at the point in said first arm farthest from said clip axis,
   (ii) a first clamping jaw positioned at one free end of said resilient member, and
   (iii) a guided element which makes a simple turn of less than 180 degrees between said first forceps-gripping elbow and said first clamping jaw; and
   a second arm having
   (i) a second flex section extending from said spring away from said clip axis to a point farthest from said clip axis then toward said clip axis so that said first flex section is disposed lengthwise along said clip axis on the opposite side of said clip axis from said first flex section, resiliently deformable from its position with respect to said clip axis, and forming a second forceps-gripping elbow at the point in said second arm farthest from said clip axis, (ii) a second clamping jaw positioned at the second free end of said resilient member, and (iii) a bent guide section positioned between said second forceps-gripping elbow and said second clamping jaw confining movement of said guided element at three points, with two of said points positioned in an essentially common plane on one side of said guided element and the third point positioned on the opposite side of said guided element, said movement of said guided element within said bent guide section confined to two degrees of freedom;

2. A surgical clip according to claim 1 wherein said first clamping jaw and said second clamping jaw are each substantially straight, are of approximately equal length, terminate at a free end of said resilient member at the same position along said clip axis, and each present flat faces toward the opposing clamping jaw for contacting and clamping tissue.

3. A surgical clip according to claim 2 wherein said resilient member is formed of a material compatible with body tissue and body fluids.

4. A surgical clip according to claim 2 wherein said resilient member is a nonmagnetic material.

5. A surgical clip according to claim 4 wherein said nonmagnetic material is titanium.

6. A surgical clip according to claim 4 wherein said nonmagnetic material is a titanium alloy.

7. A surgical clip according to claim 2 wherein said clamping jaws are symmetrically disposed on opposite sides of said clip axis when urged against one another by said coil spring.

8. A surgical clip according to claim 7 wherein each of said clamping jaws is disposed on the opposite side of said clip axis with respect to the flex section from which it extends.

9. A surgical clip according to claim 8 wherein said first flex section further includes (i) a first straight length integrally connected at one end to said coil spring, extending away from said coil spring at an oblique angle to said clip axis, and integrally connected to said first forcepsgripping elbow at its opposite end and (ii) a second straight length integrally connected at one end to said first forceps-gripping elbow and integrally connected to said guided element at its opposite end, extending toward said guided element at an oblique angle to said clip axis; and said second flex section further includes (iii) a third straight length integrally connected at one end to said coil spring, extending away from said coil spring at an oblique angle to said clip axis, and integrally connected to said second forcepsgripping elbow at its opposite end and (iv) a fourth straight length integrally connected at one end to said second forceps-gripping elbow and integrally connected to said guide section at its opposite end, extending toward said guide section at an oblique angle to said clip axis.

10. A surgical clip according to claim 9 wherein said guided element of said first arm extends through said bent guide section of said second arm.

11. A surgical clip according to claim 2 wherein the dimensions of said resilient member are sufficiently small to permit cerebral implantation.

12. A surgical clip according to claim 1 wherein said bent guide section of said second arm is open.

13. A surgical clip according to claim 12 wherein said first clamping jaw and said second clamping jaw are each substantially straight, are of approximately equal length, terminate at a free end of said resilient member at the same position along said clip axis, and each present flat faces toward the opposing clamping jaw for contacting and clamping tissue.

14. A surgical clip according to claim 13 wherein said resilient member is formed of a material compatible with body tissue and body fluids.

15. A surgical clip according to claim 13 wherein said resilient member is a nonmagnetic material.

16. A surgical clip according to claim 15 wherein said nonmagnetic material is titanium.

17. A surgical clip according to claim 15 wherein said nonmagnetic material is a titanium alloy.

18. A surgical clip according to claim 13 wherein said clamping jaws are symmetrically disposed on opposite sides of said clip axis when urged against one another by said coil spring.

19. A surgical clip according to claim 18 wherein each of said clamping jaws is disposed on the opposite side of said clip axis with respect to the flex section from which it extends.

20. A surgical clip according to claim 19 wherein said first flex section further includes (i) a first straight length integrally connected at one end to said coil spring, extending away from said coil spring at an oblique angle to said clip axis, and integrally connected to-said first forcepsgripping elbow at its opposite end and (ii) a second straight length integrally connected at one end to said first forceps-gripping elbow and integrally connected to said guided element at its opposite end, extending toward said guided element at an oblique angle to said clip axis; and said second flex section further includes (iii) a third straight length integrally connected at one end to said coil spring, extending away from said coil spring at an oblique angle to said clip axis, and integrally connected to said second forcepsgripping elbow at its opposite end and (iv) a fourth straight length integrally connected at one end to said second forceps-gripping elbow and integrally connected to said guide section at its opposite end, extending toward said guide section at an oblique angle to said clip axis.

21. A surgical clip according to claim 20 wherein said guided element of said first arm extends through said bent guide section of said second arm.

22. A surgical clip according to claim 13 wherein the dimensions of said resilient member are sufficiently small to permit cerebral implantation.

23. A surgical clip according to claim 1 wherein said bent guide section of said second arm forms a loop encircling said guided element of said first arm.

24. A surgical clip according to claim 23 wherein said loop is a flattened oval.

25. A surgical clip according to claim 24 wherein said first clamping jaw and said second clamping jaw are each substantially straight, are of approximately equal length, terminate at a free end of said resilient member at the same position along said clip axis, and each present flat faces toward the opposing clamping jaw for contacting and clamping tissue.

26. A surgical clip according to claim 25 wherein said resilient member is formed of a material compatible with body tissue and body fluids.

27. A surgical clip according to claim 25 wherein said resilient member is a nonmagnetic material.

28. A surgical clip according to claim 27 wherein said nonmagnetic material is titanium.

29. A surgical clip according to claim 27 wherein said nonmagnetic material is a titanium alloy.

30. A surgical clip according to claim 25 wherein said clamping jaws are symmetrically disposed on opposite sides of said clip axis when urged against one another by said coil spring.

31. A surgical clip according to claim 30 wherein each of said clamping jaws is disposed on the opposite side of said clip axis with respect to the flex section from which it extends.

32. A surgical clip according to claim 31 wherein said first flex section further includes
(i) a first straight length integrally connected at one end to said coil spring, extending away from said coil spring at an oblique angle to said clip axis, and integrally connected to said first forcepsgripping elbow at its opposite end and (ii) a second straight length integrally connected at one end to said first forceps-gripping elbow and integrally connected to said guided element at its opposite end, extending toward said guided element at an oblique angle to said clip axis; and
said second flex section further includes
(iii) a third straight length integrally connected at one end to said coil spring, extending away from said coil spring at an oblique angle to said clip axis, and integrally connected to said second forcepsgripping elbow at its opposite end and (iv) a fourth straight length integrally connected at one end to said second forceps-gripping elbow and integrally connected to said guide section at its opposite end, extending toward said guide section at an oblique angle to said clip axis.

33. A surgical clip according to claim 32 wherein said guided element of said first arm extends through said bent guide section of said second arm.

34. A surgical clip according to claim 33 wherein said guide section is substantially perpendicular to said clip axis at said two movement-confining points positioned in an essentially common plane on one side of said guided element.

35. A surgical clip according to claim 25 wherein the dimensions of said resilient member are sufficiently small to permit cerebral implantation.

36. A surgical clip comprising a single, continuous, resilient member formed along a clip axis without machining operations which remove material or joining operations which add material and including:
a coil spring positioned on the axis and at one end of said clip;
a first arm having
(i) a first flex section extending from said spring away from said clip axis to a point farthest from said clip axis then toward said clip axis so that said first flex section is disposed lengthwise along said clip axis, resiliently deformable from its position with respect to said clip axis, and forming a first forceps-gripping elbow at the point in said first arm farthest from said clip axis,
(ii) a first clamping jaw positioned at one free end of said resilient member, and
(iii) a guided element which makes a simple turn of less than 180 degrees between said first forceps-gripping elbow and said first clamping jaw; and
a second arm having
(i) a second flex section extending from said spring away from said clip axis to a point farthest from said clip axis then toward said clip axis so that said first flex section is disposed lengthwise along said clip axis on the opposite side of said clip axis from said first flex section, resiliently deformable from its position with respect to said clip axis, and forming a second forceps-gripping elbow at the point in said second arm farthest from said clip axis,
(ii) a second clamping jaw positioned at the second free end of said resilient member, and
(iii) a bent guide section positioned between said second forceps-gripping elbow and said second clamping jaw confining movement of said guided element at three points, with two of said points positioned in an essentially common plane on one side of said guided element and the third point positioned on the opposite side of said guided element, wherein said bent guide section is open and makes a substantially perpendicular, L-shaped pivot between the two movement-confining points positioned in an essentially common plane on one side of said guided element;
whereby said coil spring is located between said first and second flex sections urging said first and second clamping jaws against each other.

37. A surgical clip comprising a single, continuous, resilient member formed along a clip axis without machining operations which remove material or joining operations which add material and including:
a coil spring positioned on the axis and at one end of said clip;
a first arm having
(i) a first flex section extending from said spring away from said clip axis to a point farthest from said clip axis then toward said clip axis so that said first flex section is disposed lengthwise along said clip axis, resiliently deformable from its position with respect to said clip axis, and forming a first forceps-gripping elbow at the point in said first arm farthest from said clip axis,
(ii) a first clamping jaw positioned at one free end of said resilient member, and
(iii) a guided element which makes a simple turn of less than 180 degrees between said first forceps-gripping elbow and said first clamping jaw; and
a second arm having
(i) a second flex section extending from said spring away from said clip axis to a point farthest from said clip axis then toward said clip axis so that said first flex section is disposed lengthwise along said clip axis on the opposite side of said clip axis from said first flex section, resiliently deformable from its position with respect to said clip axis, and forming a second forceps-gripping elbow at the point in said second arm farthest from said clip axis,
(ii) a second clamping jaw positioned at the second free end of said resilient member, and
(iii) a bent guide section positioned between said second forceps-gripping elbow and said second clamping jaw confining movement of said guided element at three points, with two of said points positioned in an essentially common plane on one side of said guided element and the third point positioned on the opposite side of said guided element, wherein said bent guide section is open and makes a gradual loop between the two movement-confining points positioned in an essentially common plane on one side of said guided element;

whereby said coil spring is located between said first and second flex sections urging said first and second clamping jaws against each other.

38. A surgical clip according to claim 37, wherein said gradual loop is substantially C-shaped.

39. A surgical clip according to claim 37, wherein said gradual loop forms a spiral.

* * * * *

UNITED STATES PATENT AND TRADEMARK OFFICE
CERTIFICATE OF CORRECTION

PATENT NO. : 5,053,045

DATED : October 1, 1991

INVENTOR(S) : Ferenc J. Schmidt and P. Kevin Maughan

It is certified that error appears in the above-indentified patent and that said Letters Patent is hereby corrected as shown below:

On the title page, Item [56] Reference Cited delete "Furatsu" and insert --Funatsu --.

Column 2, line 24, insert --1-- before "-2 mm wide";

Column 6, line 4, delete "axis 12" and insert --axis 22 --;

Column 6, line 26, delete "element 32" and insert --element 30 --;

Column 6, line 42, delete "element 32" and insert --element 30 --;

Column 6, line 46, delete "element 32" and insert --element 30 --;

Column 6, line 49, delete "element 32" and insert --element 30 --;

UNITED STATES PATENT AND TRADEMARK OFFICE
CERTIFICATE OF CORRECTION

PATENT NO. : 5,053,045
DATED : Oct. 1, 1991
INVENTOR(S) : Ferenc J. Schmidt and P. Kevin Maughan It is certified that error appears in the above-indentified patent and that said Letters Patent is hereby corrected as shown below:

Column 6, line 62: delete "element 32" and insert --element 30--;

Column 7, line 6: delete "and 10" and insert --and 50--;

Column 7, line 48: delete "element 32" and insert --element 30--;

Column 7, line 52: delete "32" and insert --30-- (twice);

Column 8, line 8: delete "section 76" and insert --section 86--;

Column 8, line 10: delete "section 72 and second flex section 26" and insert --section 78 and second flex section 86--;

Column 8, line 11: delete "jaw 72" and insert --jaw 82--;

Column 8, line 15: delete "section 72" and insert --section 78--;

Column 8, line 20: delete "section 72" and insert --section 78--;

UNITED STATES PATENT AND TRADEMARK OFFICE
CERTIFICATE OF CORRECTION

PATENT NO. : 5,053,045

DATED : Oct. 1, 1991

INVENTOR(S) : Ferenc J. Schmidt and P. Kevin Maughan

It is certified that error appears in the above-indentified patent and that said Letters Patent is hereby corrected as shown below:

Column 8, line 23: delete "so" and insert --80--;

Column 8, line 29: delete "section 72" and insert --section 78--;

Column 8, line 34: delete "section 72" and insert --section 78--;

Column 8, line 37: delete "section 72" and insert --section 78--;

Column 8, line 40: delete "tion 76" and insert --tion 86--;

Column 8, line 47: delete "section 22" and insert --section 88--;

Column 8, line 48: delete "section 76" and insert --section 86--;

Column 8, line 63: delete "section 72" and insert --section 78--;

Column 8, line 66: delete "section 72 and jaw 72" and insert --section 78 and jaw 82--;

UNITED STATES PATENT AND TRADEMARK OFFICE
CERTIFICATE OF CORRECTION

PATENT NO. : 5,053,045

DATED : Oct. 1, 1991

INVENTOR(S) : Ferenc J. Schmidt and P. Kevin Maughan

Page 4 of 11

It is certified that error appears in the above-indentified patent and that said Letters Patent is hereby corrected as shown below:

Column 8, line 67: delete "section 72 of second arm 74" and insert --section 88 of second arm 84--;

Column 9, line 1: delete "section 78 of second arm 74" and insert --section 88 of second arm 84--;

Column 9, line 4: delete "section 72" and insert --section 88--;

Column 9, line 5: delete "Section 22" and insert --Section 88--;

Column 9, line 7: delete "section 22" and insert --section 88--;

Column 9, line 7: delete "so" and insert --80--;

Column 9, line 9: delete "so" and insert --80--;

Column 9, line 10: delete "22" and insert --88--;

Column 9, line 12: delete "so" and insert --80--;

UNITED STATES PATENT AND TRADEMARK OFFICE
CERTIFICATE OF CORRECTION

PATENT NO. : 5,053,045
DATED : Oct. 1, 1991
INVENTOR(S) : Ferenc J. Schmidt and P. Kevin Maughan It is certified that error appears in the above-indentified patent and that said Letters Patent is hereby corrected as shown below:

Column 9, line 13: delete "section 82" and insert --section 88--;

Column 9, line 14: delete "so, section 22 and element so" and insert --80, section 88 and element 80--;

Column 9, line 15: delete "so" and insert --80--;

Column 9, line 16: delete "22" and insert --88--;

Column 9, line 19: delete "section 22" and insert --section 88--;

Column 9, line 20: delete "so" and insert --80--;

Column 9, line 21: delete "22 and element so" and insert --88 and element 80--;

Column 9, line 23: delete "section 22" and insert --section 88--;

Column 9, line 25: delete "so" and insert --80--;

UNITED STATES PATENT AND TRADEMARK OFFICE
CERTIFICATE OF CORRECTION

PATENT NO. : 5,053,045

DATED : Oct. 1, 1991

INVENTOR(S) : Ferenc J. Schmidt and P. Kevin Maughan

It is certified that error appears in the above-indentified patent and that said Letters Patent is hereby corrected as shown below:

Column 9, line 29: delete "section 22" and insert --section 88--;

Column 9, line 30: delete "so" and insert --80--;

Column 9, line 36: delete "tions 72 and 16" and insert --tions 78 and 86--;

Column 9, line 40: delete "jaws 88" and insert --jaws 82--;

Column 9, line 51: delete "so" and insert --80--;

Column 9, line 54: delete "so" and insert --80--;

Column 9, line 57: delete "section 22" and insert --section 88--;

Column 9, line 58: delete "section 72" and insert --section 88--;

Column 9, line 59: delete "so. Thus, section 72" and insert --80. Thus, section 88--;

Column 10, line 2: delete "section 22" and insert --section 88--;

UNITED STATES PATENT AND TRADEMARK OFFICE
CERTIFICATE OF CORRECTION

PATENT NO. : 5,053,045
DATED : Oct. 1, 1991
INVENTOR(S) : Ferenc J. Schmidt and P. Kevin Maughan It is certified that error appears in the above-indentified patent and that said Letters Patent is hereby corrected as shown below:

Column 10, line 5: delete "section 22" and insert --section 88--;

Column 10, line 41: delete "Other" and insert --other--;

Column 10, line 64: delete "Way" and insert --way--;

Column 11, line 2: delete "length 48" and insert --length 148--;

Column 11, line 22: delete "Way" and insert --way--;

Column 11, line 50: delete "section 132" and insert --section 138--;

Column 11, line 57: delete "element 132" and insert --element 130--;

Column 11, line 58: delete "Where" and insert --where--;

Column 12, line 22: delete "Of" and insert --of--;

Column 12, line 25: delete "element 132" and insert --element 130--;

UNITED STATES PATENT AND TRADEMARK OFFICE
CERTIFICATE OF CORRECTION

PATENT NO. : 5,053,045
DATED : Oct. 1, 1991
INVENTOR(S) : Ferenc J. Schmidt and P. Kevin Maughan It is certified that error appears in the above-indentified patent and that said Letters Patent is hereby corrected as shown below:

Column 12, line 39: delete "loaner" and insert --longer--;

Column 12, line 54: delete "element 132" and insert --element 130--;

Column 12, line 65: delete "element 132" and insert --element 130--;

Column 13, line 2: delete "Figure B" and insert --FIG. 8--;

Column 13, line 26: insert --138-- after "section";

Column 13, line 44: delete "Within" and insert --within--; and

Column 13, line 67: delete "pivot 62" and insert --pivot 60--.

UNITED STATES PATENT AND TRADEMARK OFFICE
CERTIFICATE OF CORRECTION

PATENT NO. : 5,053,045

DATED : Oct. 1, 1991

INVENTOR(S) : Ferenc J. Schmidt and P. Kevin Maughan

It is certified that error appears in the above-indentified patent and that said Letters Patent is hereby corrected as shown below:

In the Claims:

Claim 1, column 15, line 16: after "to two degrees of freedom;" insert --whereby said coil spring is located between said first and second flex sections urging said first and second clamping jaws against each other.--;

Claim 9, column 15, line 47: delete "forcepsgripping" and insert --forceps-gripping--;

Claim 9, column 15, line 59: delete "forcepsgripping" and insert --forceps-gripping--;

Claim 20, column 16, line 35: delete "to-said" and insert --to said--;

Claim 20, column 16, line 35: delete "forcepsgripping" and insert --forceps-gripping--;

Claim 20, column 16, line 46: delete "forcepsgrip" and insert --forceps-grip--;

Claim 32, column 17, line 25: delete "forcepsgripping" and insert --forceps-gripping--;

Claim 32, column 17, line 36: delete "forcepsgrip" and insert --forceps-grip--;

UNITED STATES PATENT AND TRADEMARK OFFICE
CERTIFICATE OF CORRECTION

PATENT NO. : 5,053,045
DATED : Oct. 1, 1991
INVENTOR(S) : Ferenc J. Schmidt and P. Kevin Maughan It is certified that error appears in the above-indentified patent and that said Letters Patent is hereby corrected as shown below:

Claim 38, column 20, line 6: delete "37," and insert --37--; and

Claim 39, column 20, line 8: delete "37," and insert --37--.

Figure 1 and 2 should appear a shown on the attached sheet.

Signed and Sealed this

Twenty-second Day of March, 1994

Attest:

BRUCE LEHMAN

*Attesting Officer*   *Commissioner of Patents and Trademarks*